(12) United States Patent
Dupic et al.

(10) Patent No.: US 8,052,759 B2
(45) Date of Patent: Nov. 8, 2011

(54) HERNIA PROSTHESIS AND METHOD FOR FABRICATING SAME

(75) Inventors: Alexandre Dupic, La Talaudiere (FR); Patrick Carteron, Chalain le Comtal (FR); William Wiecek, Bonson (FR)

(73) Assignee: Aspide Medical, La Talaudiere (FR)

( * ) Notice: Subject to any disclaimer, the term of this patent is extended or adjusted under 35 U.S.C. 154(b) by 217 days.

(21) Appl. No.: 12/492,274

(22) Filed: Jun. 26, 2009

(65) Prior Publication Data

US 2009/0326676 A1 Dec. 31, 2009

(30) Foreign Application Priority Data

Jun. 27, 2008 (FR) .................................... 08 54306

(51) Int. Cl.
*A61F 2/02* (2006.01)
(52) U.S. Cl. .................................................. 623/23.72
(58) Field of Classification Search ............... 606/151, 606/213; 623/23.72, 23.74; 600/37
See application file for complete search history.

(56) References Cited

U.S. PATENT DOCUMENTS

| 5,147,374 A | 9/1992 | Fernandez |
| 7,785,334 B2 * | 8/2010 | Ford et al. ..................... 606/151 |
| 7,828,854 B2 * | 11/2010 | Rousseau et al. .......... 623/23.72 |
| 2007/0276484 A1 | 11/2007 | Abell et al. |

FOREIGN PATENT DOCUMENTS

| FR | 2872024 A | 12/2005 |
| WO | 2004024030 A | 3/2004 |
| WO | 2006040760 A | 4/2006 |

OTHER PUBLICATIONS

Search Report for FR0854306 dated Oct. 6, 2008.

* cited by examiner

*Primary Examiner* — Melanie Tyson
(74) *Attorney, Agent, or Firm* — Heslin Rothenberg Farley & Mesiti P.C.

(57) ABSTRACT

A hernia prosthesis includes a first portion defining a bag joined to a second portion constituting a one-piece body. A top plate of the first portion has a plurality of radial tabs around a central opening. The second portion has three distinct successive zones including a first median zone in the form of a very long sheath for introducing and securing an inserter-unfolder device. The median portion is prolonged downwards by a plurality of bands uniformly radially disposed and having bottom ends divided into two each respectively to form two tongues in a Y fastening configuration. Each tongue is fastened by its terminal end to one of the tabs. The second portion, in a top zone, beyond the sheath, comprises two very high tongues which have, in their top portion, a longitudinal slit in their width for attaching the inserter-unfolder device.

6 Claims, 2 Drawing Sheets

HERNIA PROSTHESIS AND METHOD FOR FABRICATING SAME

CROSS REFERENCE TO RELATED APPLICATIONS

This application claims priority to French application No. 0854306 filed on Jun. 27, 2008, the entire disclosure of this application being hereby incorporated herein by reference.

BACKGROUND ART

The invention relates to the technical field of prostheses commonly used for the treatment of umbilical hernias and small eventrations.

This type of prosthesis is well known, together with the inserter device associated with it. Various studies have been conducted and many related patterns have been published. Mention can be made, for example, of US 2007/0066980, WO 2004/093690, U.S. Pat. No. 7,101,381, US 2006/0282105, U.S. Pat. No. 5,258,000 and U.S. Pat. No. 3,857,395.

The prostheses thus described are prepared in the form of a bag having a neck for opening and access to the useful portion of an inserter device prepared in the form of a winged clamp for unfolding by the action of a control rod for inserting and shaping the prosthesis. This device for inserting the prosthesis is used to implant the prosthesis in situ, unfold the prosthesis, and the operator then withdraws it.

The prostheses thus described have a serious drawback related to the relative instability of the inserter device, inside the bag accommodating the prosthesis and also during its removal.

BRIEF SUMMARY OF THE INVENTION

The Applicant's approach was therefore to reflect on a novel configuration of the hernia prosthesis to solve this problem.

After various researches and tests, the Applicant has therefore designed a novel hernia prosthesis which is ideally suited to its implantation by an inserter device which has greater stability than the prosthesis, thereby allowing the ideal implantation of the prosthesis.

According to a first feature, the hernia prosthesis of the type comprising a first portion consisting of a bag defined between a bottom plate having a disc configuration, an intermediate connecting plate and a top plate having a disc shape, joined together by joining means, the top plate including a central opening forming a neck for the passage and introduction followed by the removal of a device for introducing and optimal unfolding of the prosthesis in situ is characterized in that the said first portion is joined to a second portion constituting a one-piece body, and in that the top plate comprises a plurality of radial tabs around a central opening, and in that the said body comprises three distinct successive zones, a first median zone in the form of a very long sheath for introducing and securing the inserter device, the said median portion forming a sheath being prolonged downwards by a plurality of bands uniformly radially disposed and whereof the bottom ends are divided into two each respectively to reveal two tongues in a Y fastening configuration, and in that each of these tongues is fastened by its terminal end to one of the tabs formed on the bag, and in that the body, in the top portion, beyond the sheath, comprises two very high tongues which have, in the top portion, a longitudinal slit in its width for attaching the inserter device.

These features and others will appear clearly from the rest of the description.

BRIEF DESCRIPTION OF THE DRAWING FIGURES

To clarify the subject matter of the invention illustrated in a non-limiting manner in the figures of the drawings:

FIG. 3 is an exploded plan view before assembly of the components constituting the bag portion of the prosthesis, namely

DETAILED DESCRIPTION

Figure 1:
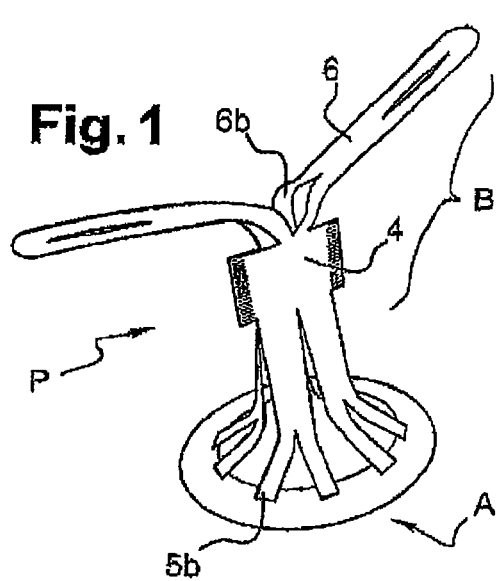
FIG. 1 is a perspective view of the prosthesis, according to the invention only.
Figure 2:
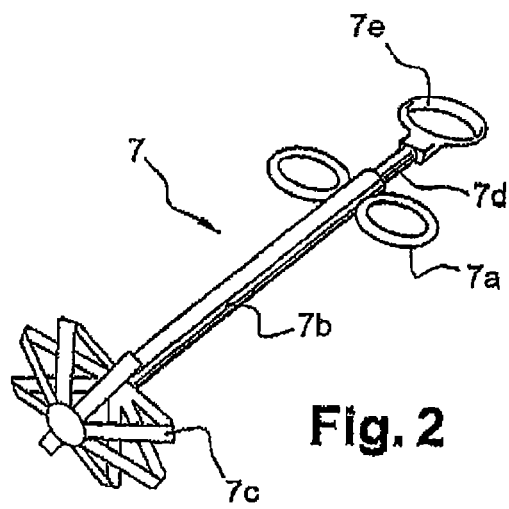
FIG. 2 is a perspective view of the inserter device.
Figure 3A:
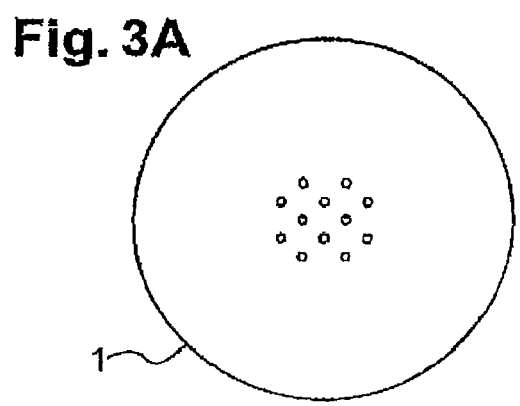
FIG. 3A is a plan view of a bottom plate.
Figure 3B:
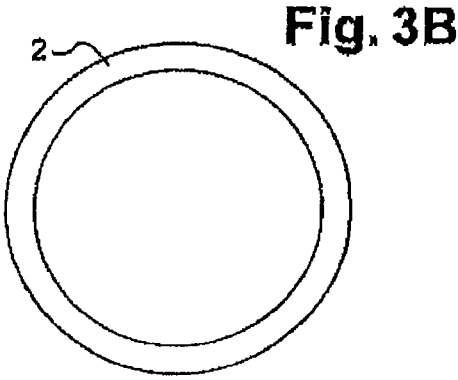
FIG. 3B is a plan view of an annular intermediate connecting plate.
Figure 3C:
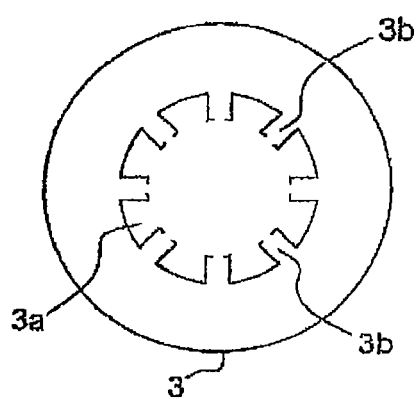
FIG. 3C is a plan view of a top plate.
Figure 4:
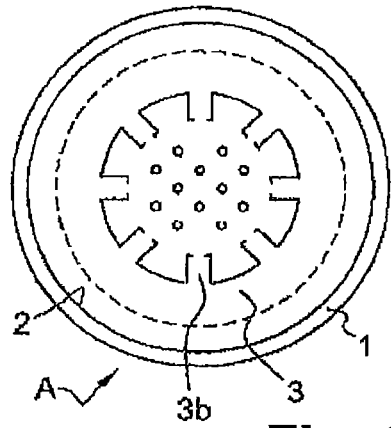
FIG. 4 is a plan view of the assembled bag portion.
Figure 6:
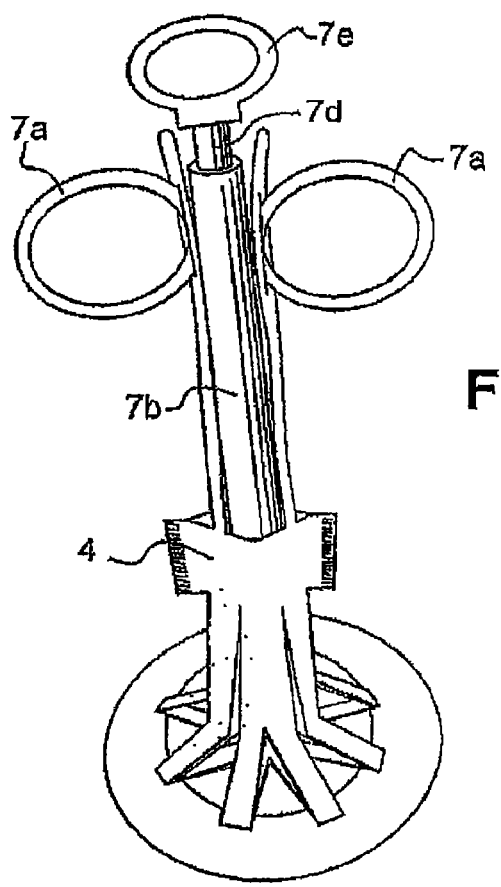
FIG. 6 is a view showing the placement of the inserter device on the prosthesis.

To make the subject matter of the invention more concrete, it is now described in a non-limiting manner in conjunction with the figures of the drawings.

The hernia prosthesis according to the invention is referred to as a whole by (P). It essentially comprises two joined portions (A-B) made from similar materials and, in particular polypropylene. The first portion (A) constitutes the bag of the prosthesis and comprises a bottom plate (1) having a disc configuration, an annular intermediate connecting plate (2) having the same configuration and disposed at the peripheral edge of the bottom plate, and a top plate (3) having a disc shape, the three components thus described being joined by welding or other joining means, at the peripheral edge. The bottom plate is solid and may, if applicable, have openings for draining the implant site. The top plate has a central opening (3a) forming a neck for the passage and insertion of the inserter device (7). The bottom plate is advantageously made from non-woven, non-knitted polypropylene, silicone treated to limit visceral adhesion, the top plate is advantageously made from knitted polypropylene, for example to favour tissue integration. The annular intermediate connecting plate is advantageously made from non-woven, non-knitted polypropylene.

In the embodiment of the invention, the top plate, around the central opening (3a) has a circular slot revealing radial tabs (3b). Preferably, the number of tabs is fixed at eight in order to distribute the forces during the retraction or unfolding of the prosthesis by the associated device. The second portion (B) constitutes a one-piece body having the function of ensuring the placement and the stability of the inserter device (7) or connection with the bag of the prosthesis. This second portion, constituting the body, is made in a single step and also from non-woven polypropylene. It comprises three distinct successive zones, a first median zone (4) in the form of a very long sheath for introducing and securing the inserter device. The median portion forming a sheath (4) is prolonged downwards by a plurality of bands (5) and, preferably four bands, uniformly and radially disposed, and whereof the bottom ends (5a) are divided into two each to respectively reveal two tongues (5b) in a Y fastening configuration. Each of these tongues is fixed by its terminal end by welding or other means to one of the tabs (3b) formed on the bag. Thus the disposition is shown of eight tabs (5b) which are spread in a Y pattern after assembly with the said tabs. Furthermore, the body comprises, in the top portion, beyond the sheath (4), two very high tongues (6) which have, in the top portion, a longitudinal slit (6a) in its width for attaching the gripping rings (7a) of the inserter device (7). These tongues are thus positioned along the outer tube (7b) of the device (7).

Figure 5:
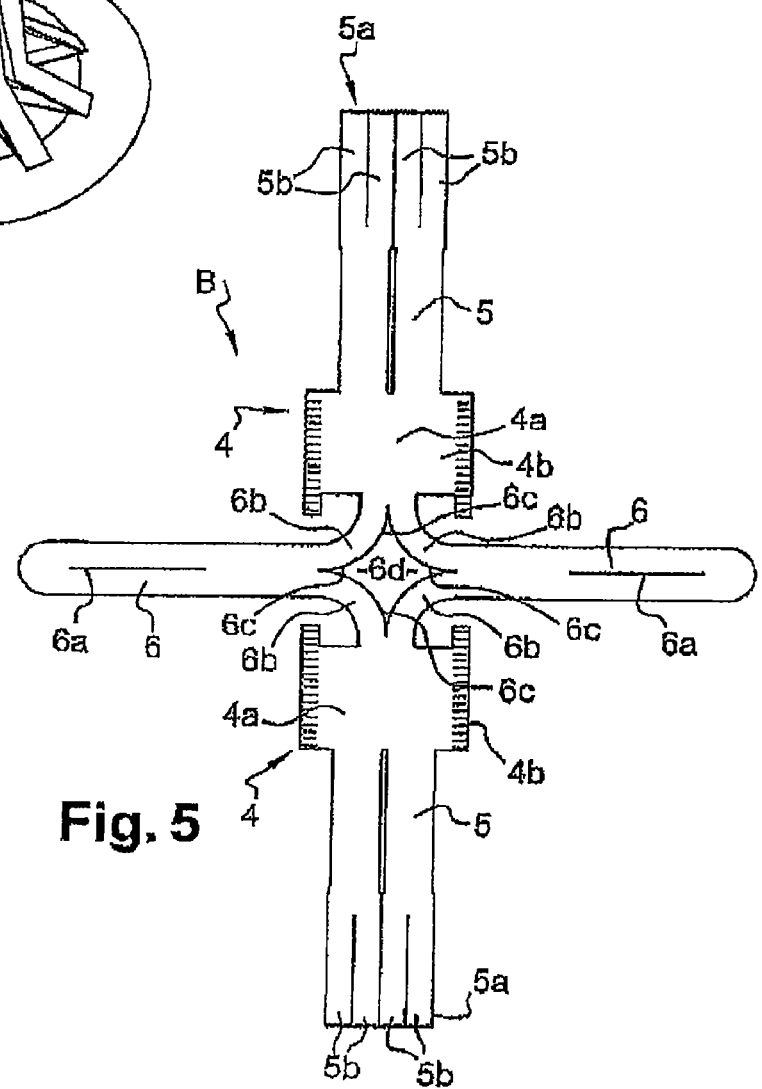
FIG. 5 is a plan view of the body portion for guiding and fastening the inserter and attachment device to the bag portion of the prosthesis.

FIG. 5 also shows, in a flat view, the configuration of the body during its fabrication. In practice, the body for guiding the inserter device and for connection to the bag is made from a plate of non-woven, non-knitted polypropylene which is precut in the flat position to the final shapes. The sheath portion (4) is made with two half-portions (4a-4b) which are then joined by welding along the junction lines (4b) provided at each end.

The bands and tongues (5 and 5b) are prepared in the longitudinal prolongation of the sheath half-portions (4a). The tongues (6) are prepared in an axis perpendicular to the sheath half-portions (4a) to reveal bent attachment tabs (6b). Thus, when the body is assembled by joining the two portions (4a) of the sheath, the tongues (6) are located in the prolongation of the junction lines of the said sheath half-portions. The base of each tongue (6) comprises two attachment tabs (6b) with a slot (6c) between them to facilitate the holding of the said tongues. A typical cross shape (6d) is thereby obtained, located above the sheath portion. This cross shape, apart from the fact that it facilitates the connection of the tongues (6) with the sheath (4), has a complementary function of securing the inserter device. Two successive zones for holding the device (7) are thereby obtained, to prevent it from tilting. The guidance of the device is thereby significantly improved. By virtue of its construction, the body is vertically stable as shown in FIG. 1 of the drawings.

The inserter device (7) comprises a tube (7b) with, at its bottom end, a plurality of prebent tongues (7c) forming a deformable parallelepiped and thereby constituting a winged clamp. A first end of the said tongues is fixed to the tube (7b) and the other end to the tip of a rod (7d) sliding in the tube. The gripping rings (7a) are provided at the top end of the tube (7b). The top end of the rod (7d) has a ring (7e) for gripping and handling. The device (7) is made from biocompatible polypropylene.

The rings (7a) join the prosthesis to the inserter-unfolder device for easy insertion of the prosthesis.

The ring (7e) allows easy handling (for example by a single hand) of the associated instrument.

As shown in FIG. 1, the body portion the body portion of the prosthesis has a large height when fully unfolded. The sheath portion (4) is located at about half of the fully unfolded body portion, and the cross portion for complementary guidance at about ⅔, from the bag, of the fully unfolded body portion. This ensures better behaviour and stability of the inserter device.

We claim:

1. Hernia prosthesis comprising a first portion including a bag defined between a bottom plate having a disc configuration, an intermediate connecting plate and a top plate having a disc shape, joined together by joining means, the top plate including a central opening forming a neck for passage and introduction followed by removal of an inserter-unfolder device for introducing the prosthesis in situ, wherein said first portion is joined to a second portion, the second portion constituting a one-piece body, the top plate comprises a plurality of radial tabs around the central opening, said second portion comprises three distinct successive zones, a first median zone having a sheath portion for introducing and securing the inserter-unfolder device, said median zone being prolonged downwards by a plurality of bands uniformly radially disposed and having bottom ends divided into two each respectively to form two tongues in a Y fastening configuration, each of the tongues being fastened at a terminal end to one of the tabs, and the second portion, in a top zone, beyond the sheath, comprises two elongated tongues having, in a top portion, a longitudinal slit in its a width of each tongue for attaching the inserter-unfolder device.

2. Hernia prosthesis according to claim 1, wherein the sheath portion comprises two half-portions joined along junction lines prepared at each end, and serves to guide the inserter-unfolder device.

3. Hernia prosthesis according to claim 2, wherein the bands and tongues are formed in a longitudinal prolongation of the sheath half-portions, and the tongues are formed in an axis perpendicular to the sheath half-portions to include bent attachment tabs.

4. Hernia prosthesis according to claim 3, wherein a base of each tongue comprises two attachment tabs with a slot between them to facilitate holding of said tongues, while defining a cross shape located above the sheath portion, and the cross shape facilitates connection of the tongues with the sheath portion and holds the inserter-unfolder device, while defining two zones for maintaining the device and preventing the device from tilting.

5. Hernia prosthesis according to claim 1, wherein the second portion of the prosthesis has rge an extended height when fully unfolded, the sheath portion is located at about a midpoint of the fully unfolded second portion, and a cross portion for complementary guidance is located at about ⅔ of the height, from the bag, of the fully unfolded body portion.

6. Method for fabricating the prosthesis according to claim 1, comprising producing, in a precut plate in a flat position, constituent shapes of said body including the sheath portion into half-portions, the bands and the tongues, and the top portion with the tongues with attachment tabs and slits for definition of a cross shape constituting, with the sheath portion, zones for holding and guiding the inserter-unfolder device and for shaping the prosthesis.

* * * * *

UNITED STATES PATENT AND TRADEMARK OFFICE
CERTIFICATE OF CORRECTION

| | |
|---|---|
| PATENT NO. | : 8,052,759 B2 |
| APPLICATION NO. | : 12/492274 |
| DATED | : November 8, 2011 |
| INVENTOR(S) | : Dupic et al. |

It is certified that error appears in the above-identified patent and that said Letters Patent is hereby corrected as shown below:

Column 4, at Claim 5, Line 41: after "second portion of the prosthesis has" Delete "rge"

Signed and Sealed this
Twenty-seventh Day of December, 2011

David J. Kappos
*Director of the United States Patent and Trademark Office*